United States Patent [19]

Raddatz et al.

[11] Patent Number: 5,120,744
[45] Date of Patent: Jun. 9, 1992

[54] SUBSTITUTED (QUINOLIN-2-YL-METHOXY)PHENYLTHI-OUREAS

[75] Inventors: Siegfried Raddatz, Cologne; Klaus Mohrs, Wuppertal; Burkhard Fugmann, Wuelfrath; Romanis Fruchtmann, Cologne; Christian Kohlsdorfer, Erftstadt; Reiner Müller-Peddinghaus; Pia Theisen-Popp, both of Bergisch Gladbach, all of Fed. Rep. of Germany

[73] Assignee: Bayer Aktiengesellschaft, Leverkusen, Fed. Rep. of Germany

[21] Appl. No.: 593,180

[22] Filed: Oct. 5, 1990

[30] Foreign Application Priority Data

Oct. 21, 1989 [DE] Fed. Rep. of Germany ....... 3935139

[51] Int. Cl.$^5$ .................. C07D 215/14; A61K 31/47
[52] U.S. Cl. ................................. 514/311; 514/312; 546/172; 546/175; 546/176
[58] Field of Search ............... 546/175, 155, 152, 153, 546/176, 178, 157, 172; 514/311, 312; 587/594

[56] References Cited

U.S. PATENT DOCUMENTS

| | | | |
|---|---|---|---|
| 4,376,202 | 3/1983 | Ura et al. | 546/157 |
| 4,425,343 | 1/1984 | Sakata et al. | 546/157 |
| 4,530,931 | 7/1985 | Musser et al. | 546/175 |
| 4,732,978 | 3/1988 | Kreft et al. | 546/153 |
| 4,769,387 | 9/1988 | Summers et al. | 546/175 |
| 4,769,461 | 9/1988 | Musser et al. | 546/153 |
| 4,826,987 | 5/1989 | Nielsen et al. | 546/174 |
| 4,839,369 | 6/1989 | Youssefyeh et al. | 546/152 |
| 4,914,098 | 4/1990 | Böger et al. | 514/311 |
| 5,045,547 | 9/1991 | Raddatz et al. | 514/312 |

FOREIGN PATENT DOCUMENTS 57-64675 4/1982 Japan.
2202223 9/1988 United Kingdom.

OTHER PUBLICATIONS

Burger, "Medicinal Chemistry" 2nd Ed. Interscience, N.Y., p. 42 (1960).
Musser et al., Jour. Med. Chem. vol. 33 No. 1 pp. 240–245 (1990).
Chemical Abstract, vol. 97, entry 1277519S, 1982.
Chemical Abstracts, vol. 97, 1982, p. 715, paragraph No. 127519j, Columbus, Ohio, US; & JP-A-82 64 675 (Nissan Chemical Industries, Ltd) Apr. 19, 1982.

Primary Examiner—Donald G. Daus
Attorney, Agent, or Firm—Sprung Horn Kramer & Woods

[57] ABSTRACT

Substituted (quinolin-2-ylmethoxy)phenyl-thio-ureas of the formula

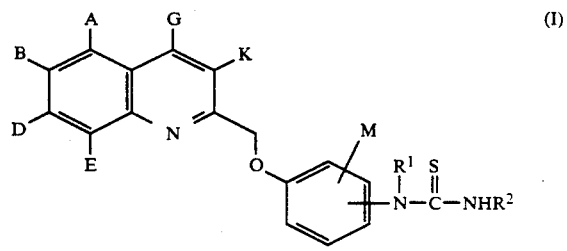

in which
A, B, D, E, G, K and M
  represent hydrogen, hydroxyl, halogen, carboxyl, nitro, trifluoromethyl or trifluoromethoxy, or
  represent alkyl, alkoxy or alkoxycarbonyl, or
  represent aryl, which is optionally substituted by halogen, hydroxyl, nitro or cyano,
$R^1$
  represents hydrogen or alkyl, which is optionally substituted by aryl or cycloalkyl, or
  represents cycloalkyl,
$R^2$
  represents alkyl, which is optionally substituted by halogen or hydroxy, or
  represents cycloalkyl, which is optionally substituted by halogen or cyano, or
  represents aryl which is optionally substituted by halogen, nitro, cyano, alkyl, or by —$SO_2$—$R^3$, in which
    $R^3$ denotes alkyl or —$NR^4R^5$, in which
      $R^4$ and $R^5$ denote hydrogen, alkyl or phenyl,
  or
$R^2$ represents —CO—$R^6$, in which
  $R^6$ denotes alkyl or aryl which is optionally substituted by halogen, nitro or cyano, and their salts, are useful for the inhibition of enzymatic reactions in the context of arachidonic acid metabolism.

5 Claims, No Drawings

SUBSTITUTED (QUINOLIN-2-YL-METHOXY)PHENYLTHIOUREAS

The invention relates to substituted (quinolin-2-yl-methoxy)phenyl-thioureas, to a process for their preparation and to their use in medicaments.

It is known that pyridylamines and quninolineamines are 5-lipoxygenase inhibitors [cf. U.S. Pat. No. 4,826,987]. Furthermore, N,N-dimethyl-N'-[3-(2-quinolyl-methoxy)phenyl-ureas are described in JP 8,264,675, Appl. 80/140,091.

Substituted (quinolin-2-ylmethoxy)phenyl-thioureas of the general formula (I)

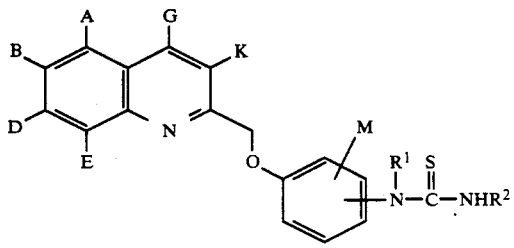

in which

A, B, D, E, G, K and M are identical or different and represent hydrogen, hydroxyl, halogen, carboxyl, nitro, trifluoromethyl or trifluoromethoxy, or represent straight-chain or branched alkyl, alkoxy or alkoxycarbonyl in each case having up to 8 carbon atoms, or represent aryl having 6 to 10 carbon atoms, which is optionally substituted by halogen, hydroxyl, nitro or cyano, $R^1$ represents hydrogen or straight-chain or branched alkyl having up to 8 carbon atoms, which is optionally substituted by aryl having 6 to 10 carbon atoms or cycloalkyl having 3 to 8 carbon atoms, or represents cycloalkyl having 3 to 8 carbon atoms, $R^2$ represents straight-chain or branched alkyl having up to 10 carbon atoms, which is optionally substituted by halogen or hydroxyl, or represents cycloalkyl having 3 to 8 carbon atoms, which is optionally substituted by halogen or cyano, or represents aryl having 6 to 10 carbon atoms, which is optionally monosubstituted to pentasubstituted by identical or different substituents from the series comprising halogen, nitro, cyano, straight-chain or branched alkyl having up to 8 carbon atoms, or by a group of the formula $-SO_2-R^3$, in which $R^3$ denotes straight-chain or branched alkyl having up to 8 carbon atoms or a group of the formula $-NR^4R^5$, in which $R^4$ and $R^5$ are identical or different and denote hydrogen, straight-chain or branched alkyl having up to 8 carbon atoms or phenyl, or $R^2$ represents a group of the formula $-CO-R^6$, in which $R^6$ denotes straight-chain or branched alkyl having up to 8 carbon atoms or aryl having 6 to 10 carbon atoms, which is optionally monosubstituted to trisubstituted by identical or different substituents from the series comprising halogen, nitro or cyano, and their salts have now been found.

In the context of the present invention, physiologically acceptable salts are preferred. Physiologically acceptable salts of the substituted (quinolin-2-yl-methoxy)phenyl-thioureas can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are additionally salts of the monovalent metals, such as alkali metals, and the ammonium salts. Sodium, potassium and ammonium salts are preferred.

Preferred compounds of the general formula (I) are those in which

A, B, D, E, G, K and M are identical or different and represent hydrogen, hydroxyl, fluorine, chlorine, bromine, trifluoromethyl, trifluoromethoxy or straight-chain or branched alkyl or alkoxy in each case having up to 6 carbon atoms, represent phenyl, which is optionally substituted by fluorine, chlorine or bromine, $R^1$ represents hydrogen or straight-chain or branched alkyl having up to 6 carbon atoms, which is optionally substituted by phenyl, $R^2$ represents straight-chain or branched alkyl having up to 8 carbon atoms, which is optionally substituted by fluorine, chlorine or bromine, or represents cyclopropyl, cyclopentyl or cyclohexyl, which is optionally substituted by fluorine, chlorine or cyano, or represents phenyl which is optionally monosubstituted to tetrasubstituted by identical or different substituents from the series comprising fluorine, chlorine, bromine, nitro, cyano, straight-chain or branched alkyl having up to 6 carbon atoms, or by a group of the formula $-SO_2-R^3$, in which $R^3$ denotes straight-chain or branched alkyl having up to 6 carbon atoms or a group of the formula $-NR^4R^5$, in which $R^4$ and $R^5$ are identical or different and denote hydrogen, straight-chain or branched alkyl having up to 6 carbon atoms or phenyl, or $R^2$ represents a group of the formula $-CO-R^6$, in which $R^6$ denotes straight-chain or branched alkyl having up to 6 carbon atoms or phenyl, which is optionally monosubstituted by identical or different substituents from the series comprising fluorine, chlorine, bromine, nitro or cyano, and their salts.

Particularly preferred compounds of the general formula (I) are those in which

A, B, D, E, G, K and M are identical or different and represent hydrogen, fluorine, chlorine, bromine, trifluoromethyl or straight-chain or branched alkyl having up to 4 carbon atoms, $R^1$ represents hydrogen or straight-chain or branched alkyl having up to 4 carbon atoms, $R^2$
represents straight-chain or branched alkyl having up to 6 carbon atoms, or represents cyclopentyl or cyclohexyl, which is optionally substituted by cyano, or represents phenyl which is optionally monosubstituted to trisubstituted by identical or different substituents from the series comprising fluorine, chlorine, bromine, nitro, cyano, straight-chain or branched alkyl having up to 4 carbon atoms, or by a group of the formula $-SO_2-R^3$, in which $R^3$ denotes straight-chain or branched alkyl having up to 4 carbon atoms or a group of the formula $-NR^4R^5$, in which $R^4$ and $R^5$ are identical or different and denote straight-chain or branched alkyl having up to 4 carbon atoms, or $R^2$ represents a group of the formula $-CO-R^6$, in which $R^6$ denotes hydrogen, straight-chain or branched alkyl having up to 4 carbon atoms or phenyl, which is optionally substituted by fluorine, chlorine or bromine, and their salts.

Very particularly preferred compounds of the general formula (I) are those in which the quinolinemethoxy grouping on the phenyl is in the 4-position to the thiourea group.

A process has additionally been found for the preparation of the compounds of the general formula (I) according to the invention

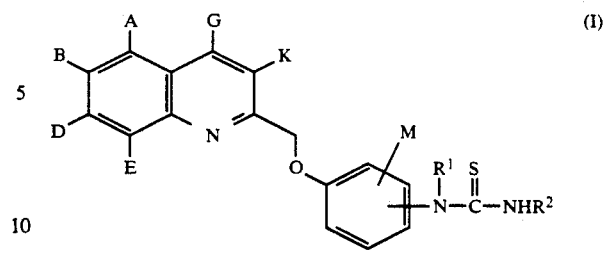

(I)

in which
A, B, D, E, G, K, M, $R^1$ and $R^2$ have the abovementioned meanings,
which is characterized in that quinolylmethoxy-anilines of the general formula (II)

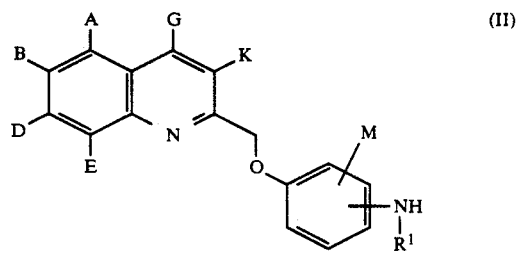

(II)

in which
A, B, D, E, G, K, M and $R^1$ have the abovementioned meanings,
are reacted with substituted isothiocyanates of the formula (III)

$$S=C=N-R^2 \qquad (III)$$

in which
$R^2$ has the abovementioned meaning,
in inert solvents.

The process according to the invention can be illustrated by the following equation:

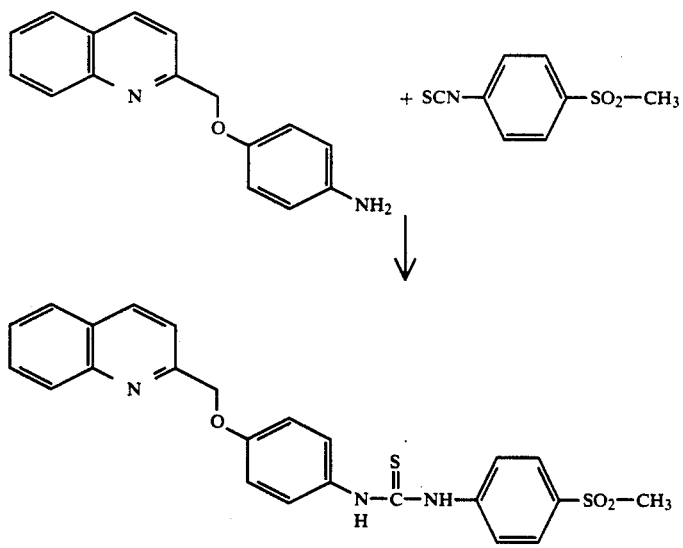

Suitable solvents for the reaction with isothiocyanates (III) are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone, nitromethane or nitroethane. It is also possible to use mixtures of the solvents mentioned. Nitromethane, nitroethane and dichloromethane are particularly preferred.

The process is in general carried out in the temperature range from 0° C. to +80° C., preferably at room temperature.

The process is in general carried out at normal pressure. However, it is also possible to carry out the process at reduced pressure or at elevated pressure (for example in a range from 0.5 to 5 bar).

In general, 1 to 3 moles, preferably 1 to 2 moles, particularly preferably 1 mole, of isothiocyanate is employed, relative to 1 mole of the amine.

The amines of the general formula (II) are known per se or can be prepared by known methods [cf. German Offenlegungsschrift DE 3,607,382 which is equivalent to U.S. Pat. No. 4,826,987].

The isothiocyanates of the general formula (III) are known per se or can be prepared by a customary method [cf. Beilstein 12, 453, Fieser 1, 844, 2, 323; Ann. Biochem. 67, 392 (1975); Indian J. Pharm. Sci. 48 (3), 53–59; Collect. Czech. Chem. Commun. 39 (1), 182–184; 38 (12), 3852–3856; J. Antibiot., 21 (8), 504–508 (Tokyo)].

The substituted (quinolin-2-yl-methoxy)phenylthioureas according to the invention can be employed as active compounds in medicaments. The substances can act as inhibitors of enzymatic reactions in the context of arachidonic acid metabolism, in particular lipoxygenase.

They are thus preferably suitable for the treatment and prevention of disorders of the airways such as allergies/asthma, bronchitis, emphysema, shock lung, pulmonary hypertension, inflammations/rheumatism and oedemas, thromboses and thromboembolisms, ischaemias (peripheral, cardiac and cerebral circulatory disturbances), cardiac and cerebral infarcts, cardiac arrhythmias, angina pectoris, arteriosclerosis, in tissue transplants, dermatoses such as psoriasis, inflammatory dermatoses, for example eczema, dermatophyte infections, infections of the skin by bacteria, metastases and for cytoprotection in the gastrointestinal tract.

The substituted (quinolin-2-yl-methoxy)phenyl-thioureas according to the invention can be used both in human medicine and in veterinary medicine.

The pharmacological activity data of the substances according to the invention are determined by the following method:

As a measure of the lipoxygenase inhibition, the release of leukotriene B4 (LTB4) from polymorphonuclear rat leukocytes (PMN) was determined by means of reverse phase HPLC according to Borgeat, P. et al., Proc. Nat. Acad. Sci. 76, 2148–2152 (1979) after adding substances and Ca ionophore. The in vivo activity of the compounds was determined using the mouse ear inflammation model according to Young, J. M. et al., J. of Investigative Dermatology 82, 367–371, (1984).

The values for some compounds according to the invention obtained by this test are shown by way of example in Table 1:

TABLE 1

| Example | LO inhibition $IC_{50}$ ($\mu m$) |
|---------|-----------------------------------|
| 3       | 0.036                             |
| 4       | 0.033                             |
| 5       | 0.41                              |
| 6       | 0.36                              |
| 7       | 0.24                              |
| 8       | 0.29                              |

The new active compounds can be converted in a manner known per se into the customary formulations, such as tablets, capsules, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight, preferably 10 to 70% by weight, in the preparation, i.e. in amounts which are sufficient in order to achieve the dosage range indicated.

The formulations are prepared, for example, by extending the active compounds with solvents and/or excipients, if appropriate using emulsifiers and/or dispersants, it being possible, for example, in the case of the use of water as a diluent, to use, if appropriate, organic solvents as auxiliary solvents.

Examples of auxiliaries which may be mentioned are: water, non-toxic organic solvents, such as paraffins (for example mineral oil fractions), vegetable oils (for example groundnut/sesame oil), alcohols (for example: ethyl) alcohol, glycerol), glycols (for example propylene glycol, polyethylene glycol), solid excipients, such as ground natural minerals (for example, kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium laurylsulphate).

Administration is carried out in a customary manner, preferably orally or parenterally, in particular perlingually or intravenously. In the case of oral administration, tablets can of course also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium laurylsulphate and talc can additionally be used for tabletting. In the case of aqueous suspensions and/or elixirs, various flavor enhancers or colorants may be added to the active compounds in addition to the abovementioned auxiliaries.

In the case of parenteral administration, solutions of the active compounds can be employed using suitable liquid excipient materials.

In general, it has proved advantageous on intravenous administration to administer amounts of about 0.01 to 10 mg/kg, preferably about 0.01 to 5 mg/kg of body weight to attain effective results. On oral administration the dosage is in general about 0.1 to 200 mg/kg, preferably 1 to 100 mg/kg of body weight.

In spite of this it may be necessary to deviate from the amounts mentioned, depending in particular on the body weight or the type of administration route, on individual behavior towards the medicament, the manner of its formulation and the point in time or interval at which administration takes place. Thus, in some cases it may be sufficient to manage with less than the minimum amount previously mentioned, while in other cases the upper limit mentioned must be exceeded. In the case of the administration of relatively large amounts, it may be advisable to divide these into a number of individual doses over the course of the day.

STARTING COMPOUND

EXAMPLE I 2-(4-Aminophenoxymethyl)quinoline

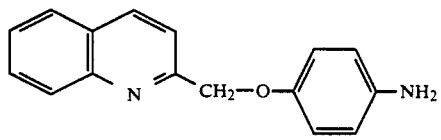

117.8 g (0.42 mol) of 2-(4-nitrophenoxymethyl)quinoline were dissolved in 1 l of methanol/tetrahydrofuran (1:1). About 5 g of Raney nickel were added and the mixture was warmed to 35° C. 63.1 g (1.26 mol) of hydrazine hydrate were then added dropwise and the mixture was stirred overnight. The residue was filtered off, the solution was concentrated in vacuo and the residue was taken up with methylene chloride. The solution was then washed with water and conc. hydrochloric acid was added to the organic phase. The precipitate which deposited was filtered off, washed with 2N hydrochloric acid and dissolved in water, and the solution was rendered alkaline with 20% strength NaOH. The residue was dried in vacuo.

Yield: 88.0 g (92.1% of theory)
M.p. = 131° C.

PREPARATION EXAMPLES (FORMULA I)

EXAMPLE 1

N-(4-Aminosulphonylphenyl)-N'-4-(quinolin-2-yl-methoxy)phenyl-thiourea

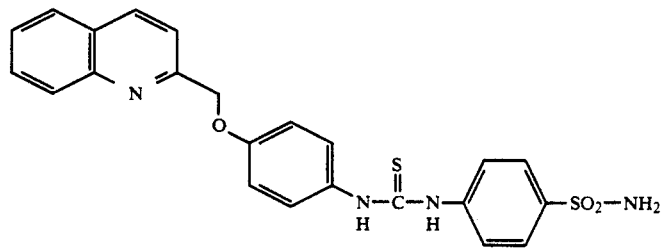

2.5 g (0.01 mol) of the compound from Example I were dissolved in 300 ml of nitroethane and 2.14 g (0.01 mol) of 4-aminosulphonylphenyl-isothiocyanate, dissolved in 300 ml of nitroethane, were added. The mixture was additionally stirred overnight at room temperature and the precipitate was then filtered off. Yield: 4.5 g (97.0 % of theory) of colorless crystals.

M.p.: 211° C.

EXAMPLE 2

N-(4-Mesylphenyl)-N'-4-(quinolin-2-yl-methoxy)phenyl-thiourea

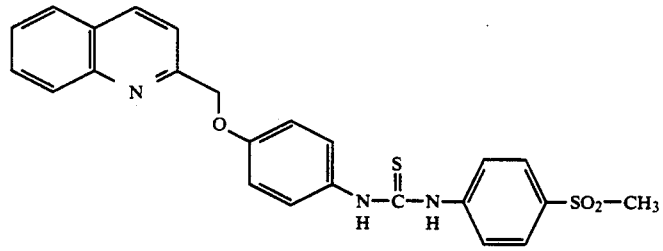

The title compound is prepared in analogy to Example 1 from 2.5 g (0.01 mol) of 2-(4-aminophenoxymethyl)-quinoline and 2.13 g (0.01 mol) of 4-mesylphenyl-isothiocyanate, in each case in 100 ml of dichloromethane.

Yield: 4 g (86.3% of theory) of colorless crystals.
M.p.: 181° C. (dec.).

EXAMPLE 3

N-(2-Methyl-4-nitrophenyl)-N'-4-(quinolin-2-yl-methoxy)phenyl-thiourea

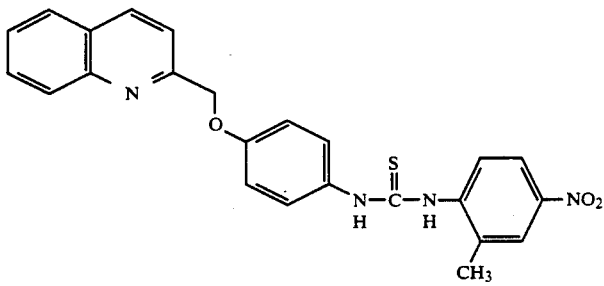

The title compound is prepared in analogy to Example 1 from 2.5 g (0.01 mol) of 2-(4-aminophenoxymethyl)-quinoline and 1.94 g (0.01 mol) of 2-methyl-4-nitrophenyl-isothiocyanate, in each case in 50 ml of dichloromethane.

Yield: 3.6 g (81.1% of theory) of yellow crystals.
M.p.: 154° C. (dec.).

EXAMPLE 4

N-(2-Methyl-4-nitro-5-chlorophenyl)-N'-4-(quinolin-2-yl-methyloxy)phenyl-thiourea

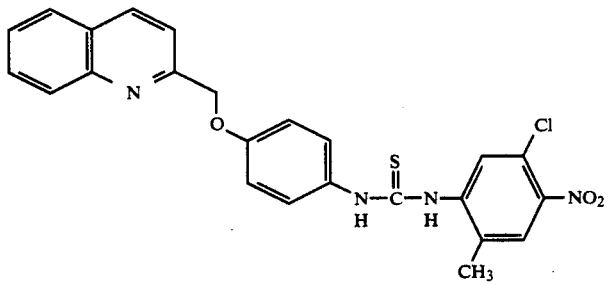

The title compound is prepared in analogy to Example 1 from 2.5 g (0.01 mol) of 2-(4-aminophenoxymethyl)-quinoline and 2.3 g (0.01 mol) of 2-methyl-4-nitro-5-chlorophenyl-isothiocyanate, in each case in 100 ml of dichloromethane.

Yield: 3.8 g (79.4% of theory) of yellow crystals.
M.p.: 169°–170° C. (dec.) recrystallized from ethyl acetate/petroleum ether.

EXAMPLE 5

N-(2-methyl-4,5-dichlorophenyl-N'-4-(quinolin-2-yl-methoxy)phenyl-thiourea

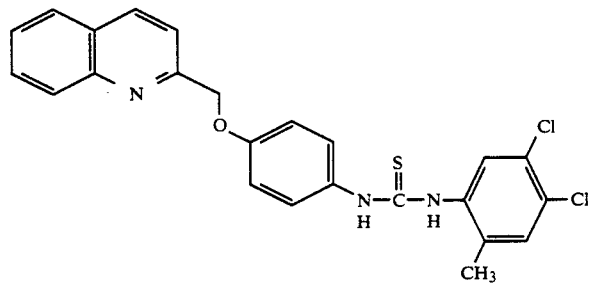

The title compound is prepared in analogy to Example 1 from 4.6 g (0.0184 mol) of 2-(4-aminophenoxymethyl)-quinoline and 4 g (0.018 mol) of 2-methyl-4,5-dichlorophenyl-isothiocyanate, in each case in 100 ml of dichloromethane.

Yield: 7.4 g (87.8% of theory) of colorless crystals.

M.p.: 175°–176° C.

EXAMPLE 6

N-(4-Chlorobenzoyl)-N'-4-(quinolin-2-yl-methoxy)-phenyl-thiourea

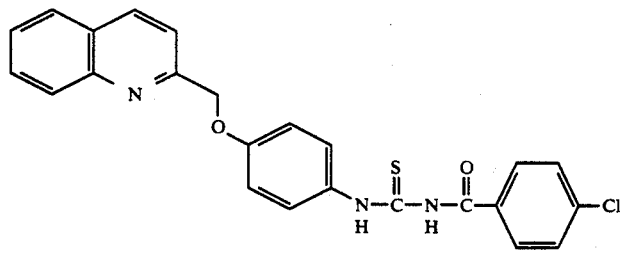

The title compound is prepared in analogy to Example 1 from 5.67 g (0.0227 mol) of 2-(4-aminophenoxymethyl)-quinoline and 4.48 g (0.0227 mol) of 4-chlorobenzoyl isothiocyanate, in each case in 100 ml of dichloromethane.

Yield: 6 g (59.3% of theory) of pale yellow crystals.
M.p.: 193°–194° C. (dec.).

EXAMPLE 7

N-(1-Cyano-cyclohexyl)-N'-4-(quinolin-2-yl-methoxy)-phenyl-thiourea

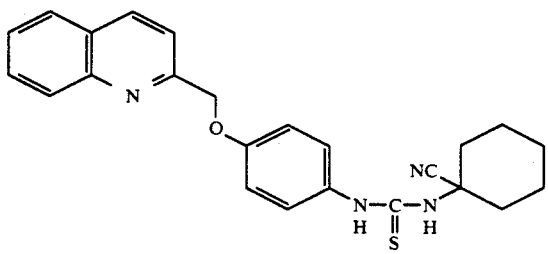

The title compound is prepared in analogy to Example 1 from 3 g (0.012 mol) of 2-(4-amino-phenoxymethyl)-quinoline and 2 g (0.012 mol) of 1-cyano-1-isothiocyanatocyclohexane, in each case in 50 ml of dichloromethane.

Yield: 3.9 g (78.1% of theory) of colorless crystals.
M.p.: 213° C. (dec.).

EXAMPLE 8

N-(2-Methyl-4-chlorophenyl)-N'-4-(quinolin-2-yl-methoxy)phenyl-thiourea

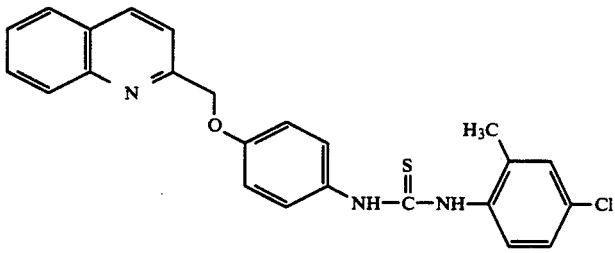

The title compound was prepared in analogy to the procedure of Examples 4 and 5.
M.p.: 148°–150° C.

What is claimed is:

1. A substituted (quinolin-2-yl-methoxy)phenyl-thiourea of the formula

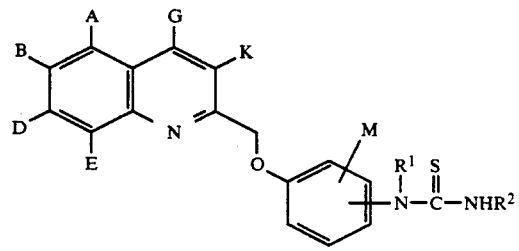

(I)

in which
A, B, D, E, G, K and M are identical or different and represent hydrogen, fluorine, chlorine, bromine, trifluoromethyl or straight-chain or branched alkyl having up to 4 carbon atoms, $R^1$ represents hydrogen or straight-chain or branched alkyl having up to 4 carbon atoms, $R^2$
represents straight-chain or branched alkyl having up to 6 carbon atoms, or
represents cyclopentyl or cyclohexyl, which is unsubstituted or substituted by cyano, or
represents phenyl which is unsubstituted or monosubstituted to trisubstituted by identical or different substituents selected from the group consisting of fluorine, chlorine, bromine, cyano, straight-chain or branched alkyl having up to 4 carbon atoms, or by nitro or a group of the formula —$SO_2$—$R^3$, in which $R^3$ denotes straight-chain or branched alkyl having up to 4 carbon atoms or a group of the formula —$NR^4R^5$, in which $R^4$ and $R^5$ are identical or different and denote hydrogen, straight-chain or branched alkyl having up to 4 carbon atoms, or
$R^2$ represents a group of the formula —CO—$R^6$, in which $R^6$ denotes straight-chain or branched alkyl having up to 4 carbon atoms or phenyl, which is unsubstituted or substituted by fluorine, chlorine or bromine,
or a physiologically acceptable salt thereof with an acid, monovalent metal, or ammonium.

2. A substituted (quinolin-2-yl-methoxy)phenyl-thiourea according to claim 1, which is
N-(4-Aminosulphonylphenyl)-N'-4-(quinolin-2-yl-methoxy)phenyl-thiourea;

N-(4-Mesylphenyl)-N'-4-(quinolin-2-yl-methoxy)phenyl-thiourea;
N-(2-Methyl-4-nitrophenyl)-N'-4-(quinolin-2-yl-methoxy)phenyl-thiourea;

N-(2-Methyl-4-nitro-5-chlorophenyl)-N'-4-(quinolin-2-yl-methoxy)phenyl-thiourea;
N-(2-methyl-4,5-dichlorophenyl-N'-4-(quinolin-2-yl-methoxy)phenyl-thiourea;
N-(4-Chlorobenzoyl)-N'-4-(quinolin-2-yl-methoxy)-phenyl-thiourea;

N-(1-Cyano-cyclohexyl)-N'-4-(quinolin-2-yl-methoxy)-phenyl-thiourea; or
N-(2-Methyl-4-chlorophenyl)-N'-4-(quinolin-2-yl-methoxy)phenyl-thiourea.

3. A substituted (quinolin-2-yl-methoxy)phenyl-thiourea according to claim 2, which is N-(2-methyl-4-nitrophenyl)-N'-4-(quinolin-2-yl-methoxy)-phenyl-thiourea, having the formula

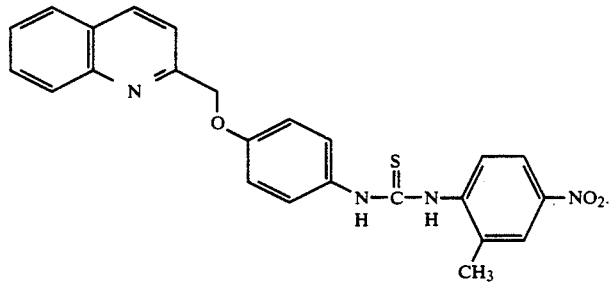

4. A substituted (quinolin-2-yl-methoxy)phenyl-thiourea according to claim 2, which is N-(2-methyl-4-nitro-5-chlorophenyl)-N'-4-(quinolin-2-yl-methoxy)phenyl-thiourea having the formula

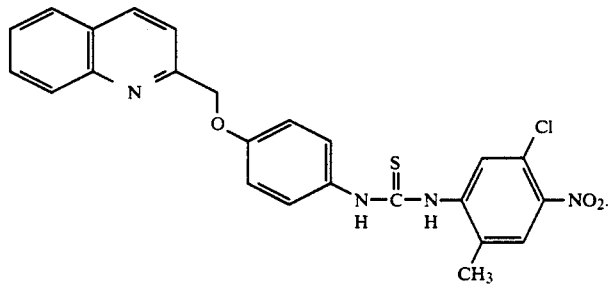

5. A composition useful to combat diseases that are susceptible to the action of lipoxygenase inhibitors, which comprises a pharmaceutically acceptable excipient and a lipoxygenase inhibiting effective amount of a substituted (quinolin-2-yl-methoxy)phenyl-thiourea according to claim 1 or a physiologically acceptable salt thereof.

* * * * *